(12) United States Patent
Zlotnick

(10) Patent No.: US 7,329,485 B2
(45) Date of Patent: Feb. 12, 2008

(54) METHODS FOR DETECTING COMPOUNDS THAT INTERFERE WITH PROTEIN AGGREGATION UTILIZING AN IN VITRO FLUORESCENCE-BASED ASSAY

(75) Inventor: Adam Zlotnick, Norman, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 11/546,796

(22) Filed: Oct. 12, 2006

(65) Prior Publication Data
US 2007/0082359 A1    Apr. 12, 2007

Related U.S. Application Data

(60) Provisional application No. 60/725,940, filed on Oct. 12, 2005.

(51) Int. Cl.
*C12Q 1/00* (2006.01)
(52) U.S. Cl. ........................................ 435/4
(58) Field of Classification Search ............ None
See application file for complete search history.

(56) References Cited

U.S. PATENT DOCUMENTS

| | | |
|---|---|---|
| 6,593,103 B1 | 7/2003 | Lingappa et al. |
| 6,849,429 B1 | 2/2005 | Watowich et al. |
| 7,105,307 B2 | 9/2006 | Colyer et al. |
| 2005/0009185 A1 | 1/2005 | Schaller et al. |

OTHER PUBLICATIONS

Andrawiss et al., Murine Leukemia Virus Particle Assembly Quantitated by Fluorescence Microscopy: Role of Gag-Gag Interactions and Membrane Association, Journal of Virology, Nov. 2003, vol. 77, No. 21, p. 11651-11660.*

Caldentey et al., Purification and characterization of the assembly factor P17 of the lipid-containing bacteriophage PRD1, European Journal of Biochemistry, 1999, 260:549-558.*

Zlotnick et al., A Small Molecule Inhibits and Misdirects Assembly of Hepatitis B Virus Capsids, Journal of Virology, May 2002, vol. 76, No. 10, pp. 4848-4854.*

Lindsey et al., Flourescent labeling of histone H3: effect on histone-histone interaction and core particle assembly, FEBS, 1985, 192(2): 230-234.*

* cited by examiner

*Primary Examiner*—Bruce R. Campell
*Assistant Examiner*—Nicole E. Kinsey
(74) *Attorney, Agent, or Firm*—Dunlap, Codding & Rogers, P.C.

(57) ABSTRACT

Methods of identifying a compound that inhibit, enhance and/or misdirect assembly of a viral capsid include providing fluorescently-labeled capsid polypeptides labeled with a fluorescent dye that changes fluorescence at high concentration, wherein assembly of the capsid polypeptides into the viral capsid results in juxtaposition of at least one of the N-terminus and C-terminus of the capsid polypeptides. In vitro assembly reactions are performed utilizing the labeled capsid polypeptide in the presence of the at least one test compound, and an amount of fluorescence is detected at at least one time point following induction of assembly, wherein the induction of assembly is detected as a change in the fluorescence of the sample. It is then determined whether the change in fluorescence detected in the presence of the at least one test compound following induction of assembly is decreased, increased, or occurs at a fast rate when compared to the fluorescence detected in the absence of the at least one test compound, wherein such decrease is an indication that the at least one test compound interferes with assembly of the viral capsid.

18 Claims, 5 Drawing Sheets

METHODS FOR DETECTING COMPOUNDS THAT INTERFERE WITH PROTEIN AGGREGATION UTILIZING AN IN VITRO FLUORESCENCE-BASED ASSAY

CROSS REFERENCE TO RELATED APPLICATIONS

This application claims benefit under 35 U.S.C. 119(e) of provisional application U.S. Ser. No. 60/725,940, filed Oct. 12, 2005, the contents of which are hereby expressly incorporated herein by reference in their entirety.

STATEMENT REGARDING FEDERALLY SPONSORED RESEARCH OR DEVELOPMENT

The government has certain rights in the present invention pursuant to a grant from the National Institutes of Health (1R01-AI067417-01) and a grant from the American Cancer Society (RSG-99-339-04-MBC).

BACKGROUND OF THE INVENTION

1. Field of the Invention

The present invention is related to a method for detecting compounds that inhibit protein aggregation, wherein the method utilizes an in vitro fluorescence-based assay. The method of the present invention identifies compounds that have potential against deleterious conditions wherein protein aggregation is important to the pathology or function of the condition. In one embodiment, the present invention is related to a method for detecting compounds that inhibit viral assembly, thus identifying potential antiviral compounds.

2. Description of the Background Art

A virus is a disease-causing agent that contains nucleic acid and can alternate between an intracellular state and an extracellular state; however, viruses require a host cell's machinery for protein synthesis and therefore can only multiply in an intracellular state. In either state, viruses are submicroscopic particles containing either deoxyribonucleic acid (DNA) or ribonucleic acid (RNA) surrounded by protein and occasionally containing other components. Viruses can vary widely in size, shape, chemical composition, range of organisms attacked, kinds of cell damage induced, and range of genetic capabilities. Viruses are known to infect animals, plants, bacteria, and fungi.

The structures (size and shape) of viruses are exceedingly diverse. The internal structure of viruses, however, generally has the nucleic acid located in the center surrounded by a protein coat called the capsid. The individual proteins that make up the capsid are called protein subunits, or capsomeres.

Replication of viruses requires that the virus induce a living cell of a host organism to make more of the essential components needed by the virus particle for growth. These components must then be assembled in the proper order, and the new virus particles must escape from the cell and infect other cells. The various phases of this replication process can be summarized as: 1) attachment (adsorption) of a virus particle to a sensitive cell; 2) penetration into the cell by the virus or its nucleic acid; 3) replication of the viral nucleic acid; 4) production of capsid protein and other essential viral constituents; 5) assembly of nucleic acid and capsid protein into new virus particles (or packaging of the virus particle); and 6) release of mature virus particles from the cell.

Given the severity of many viral infections in all types of hosts, a need always exists for new methods of treating and/or preventing deleterious viral infections. Based on the life cycle described herein before, one should be able to attack the progression of viral infection in an animal, plant, bacteria or fungi by interfering with (or inhibiting) any of the stages of the viral life cycle essential to viral infection or replication. Examination of particular viruses could lead to the discovery of such methods, which in turn could lead to the elucidation of a method applicable to all or nearly all viruses.

Most antiviral agents available today are traditional enzyme inhibitors. These include nucleotide analogs that affect replication (e.g., acylcovir and AZT) and protease inhibitors that affect processing of viral polyproteins. There are also polio- and rhinovirus specific small molecules that function by stabilizing the capsid, inhibiting release of viral nucleic acid.

Since the protein coat (also referred to interchangeably herein as a "capsid") of viruses is critical to virus propagation, compounds that interfere with normal assembly of the viral protein coat, either by inhibiting assembly or inappropriately enhancing assembly (including but not limited to, accelerating assembly kinetics, stabilizing capsids, and misdirecting assembly), would potentially function as antiviral compounds. However, prior to the present invention, an appropriate assay has not been available for identifying compounds that inhibit, enhance and/or misdirect viral coat assembly. It is to such method of detecting compounds that interfere with viral coat assembly, in a sensitive and reproducible in vitro format that is compatible with high throughput screening, that the present invention is directed.

SUMMARY OF THE PRESENT INVENTION

The present invention relates to methods of identifying a compound that interferes with assembly of a viral capsid. The interference may be by inhibiting assembly, inappropriately enhancing assembly, or misdirecting assembly of the viral capsid.

The methods include providing capsid polypeptides labeled with a fluorescent dye that changes fluorescence at high concentration (such as when two molecules of the fluorescent dye are in close proximity to one another), wherein assembly of the capsid polypeptides into the viral capsid results in juxtaposition of at at least one of the N-terminus and C-terminus of the capsid polypeptides, and wherein the fluorescent dye is attached to the at least one N-terminus and C-terminus of the capsid polypeptide. At least one test compound is provided, and an in vitro assembly reaction is performed utilizing the labeled capsid polypeptide in the presence of the at least one test compound. Then, an amount of fluorescence is detected at least one time point following induction of assembly in the presence of the at least one test compound, wherein the induction of assembly is detected as a change in the fluorescence of the sample. Then, it is determined whether the change in fluorescence detected in the presence of the at least one test compound following induction of assembly is affected when compared to the fluorescence detected in the absence of the at least one test compound, wherein such effect is an indication that the at least one test compound interferes with assembly of the viral capsid. When the change in fluorescence is decreased, such decrease is an indication that the at least one test compound inhibits assembly of the viral capsid; when the change in fluorescence is increased, such increase is an indication that the at least one test compound inappropriately enhances or misdirects assembly of the viral capsid.

In an alternative embodiment, the methods are conducted as described herein above, except that the amount of fluorescence is detected at two or more time points following induction of assembly in the presence of at least one test compound, and it is determined whether the change in fluorescence detected in the presence of at least one test compound following induction of assembly occurs at a faster rate when compared to the fluorescence detected in the absence of the at least one test compound, wherein such increased rate is an indication that the at least one test compound misdirects assembly of the viral capsid.

In one embodiment, the induction of assembly may be detected as a decrease in fluorescence of the sample.

In one embodiment, multiple test compounds are provided and screened simultaneously.

In one embodiment, the capsid polypeptide may be a recombinant polypeptide. The recombinant capsid polypeptide may be genetically modified to enable labeling thereof. For example but not by way of limitation, the recombinant capsid polypeptide may be genetically modified to include a cysteine residue on the N- or C-terminus thereof such that the at least one terminus of the recombinant capsid polypeptide that are in close proximity to one another when assembled into the capsid is provided with the cysteine residue thereon. In one embodiment, at least one other cysteine present in the recombinant capsid polypeptide may be mutated so that it does not interfere with labeling of the modified cysteine.

The present invention is also related to kits for use in methods of identifying a compound that interferes with assembly of a viral capsid. Such kit may include labeled capsid polypeptide as described herein above. In another embodiment, the kit may further include at least one of pre-blocked plates (such as but not limited to, pre-blocked black 96-well plates), labeled protein, dilution buffer (such as but not limited to, 50 mM HEPES, pH 7.5, or similar low ionic strength buffer), weak assembly buffer to preferentially search for assembly enhancers (such as but not limited to, dilution buffer plus 300 mM NaCl sufficient to obtain approximately 25% assembly), strong assembly buffer to preferentially search for assembly inhibitors (such as but not limited to, dilution buffer plus 600 mM NaCl), 100% assembly buffer (such as but not limited to, dilution buffer plus 2 M NaCl), and controls for enhancers (such as but not limited to, HAP1) and inhibitors (such as but not limited to, urea).

Other objects, features and advantages of the present invention will become apparent from the following detailed description when read in conjunction with the accompanying figures and appended claims.

DETAILED DESCRIPTION OF THE INVENTION

Figure 1:
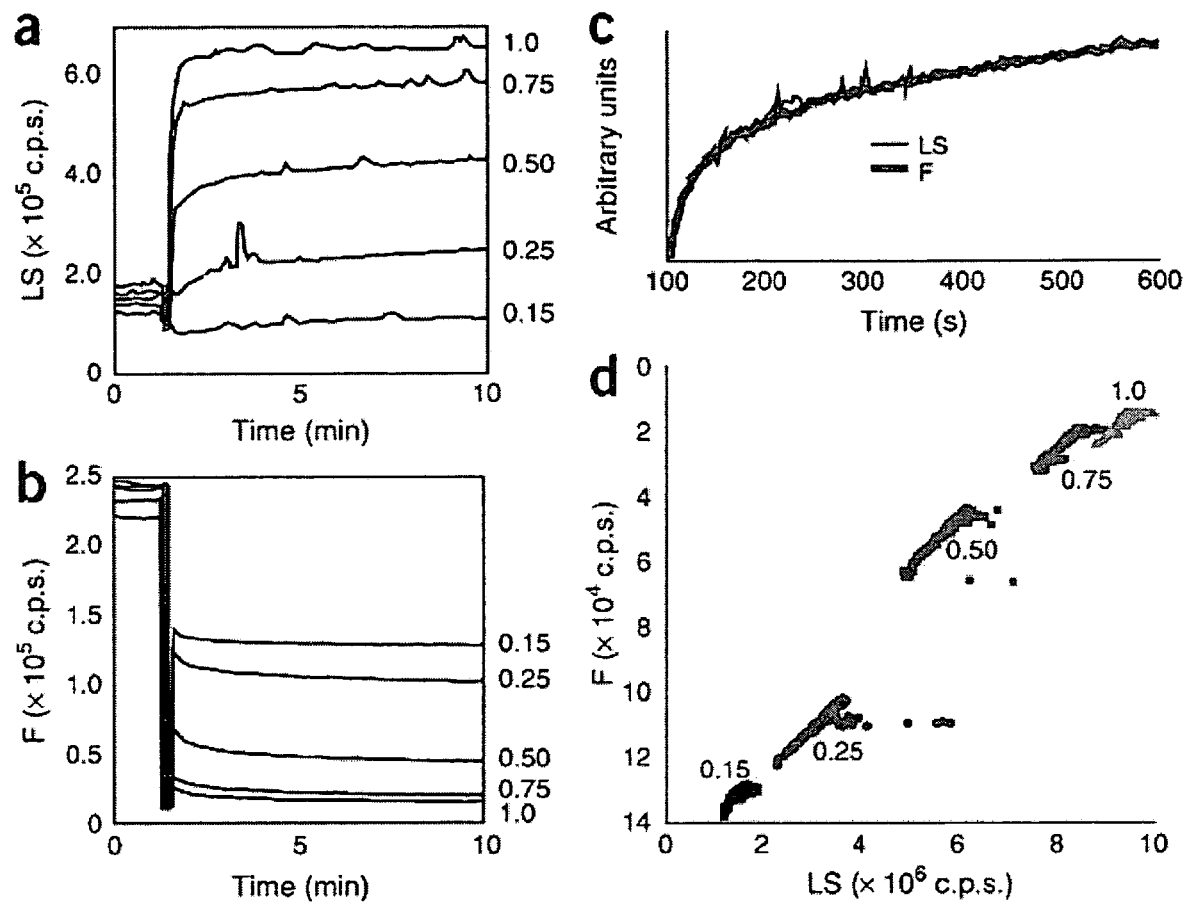
FIG. 1 illustrates the strong correlation of real-time light scattering and fluorescence signals for assembly of BODIPY-FL-labeled C150. (a) Assembly of 3 µM C150BO was measured by 90° light scattering at 21° C. All measurements were carried out in a cuvette. Assembly was initiated manually at 90 s. Final NaCl concentrations (M) are indicated to the right of the panel. (b) Assembly monitored by fluorescence (excitation at 504 nm, emission at 509 nm). Final NaCl concentrations (M) are indicated to the right of the panel. (d) Alignment of light scattering and fluorescence signals from assembly reactions at 0.25 M NaCl (data from panels a and b). To allow direct comparison, fluorescence data was rescaled by applying the linear best fit of light scattering versus fluorescence curve to the primary fluorescence data. Note that the scale for fluorescence has been inverted. (c) Comparison of fluorescence and light scattering from 100-500 s of assembly reactions using different NaCl concentrations. Final NaCl concentration (M) is indicated next to each data set. Note that the fluorescence scale has been inverted. Points lying off the diagonal correspond to peaks in light scattering probably caused by dust contaminants. LS, light scattering; F, fluorescence; c.p.s., counts per second.

Before explaining at least one embodiment of the invention in detail by way of exemplary drawings, experimentation, results, and laboratory procedures, it is to be understood that the invention is not limited in its application to the details of construction and the arrangement of the components set forth in the following description or illustrated in the drawings, experimentation and/or results. The invention is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual ($2^{nd}$ ed., Cold Spring Harbor Laboratory Press, Cold Spring Harbor, N.Y. (1989) and Coligan et al. Current Protocols in Immunology (Current Protocols, Wiley Interscience (1994)), which are incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

The terms "capsid", "virus capsid", "viral capsid", "viral protein coat" and grammatical equivalents thereof are used herein interchangeably and will be understood to refer to the protein coat or closed shell that surrounds the infective nucleic acid in virus particles. The capsid comprises numerous regularly arranged subunits.

The terms "capsomer", "capsomere", "capsid protein", "capsid polypeptide", and grammatical equivalents thereof are used herein interchangeably to refer to one of the subunits from which a virus shell or capsid is constructed. The virus capsid is formed by assembling capsomeres about the nucleic acid core in a precise geometrical pattern.

The terms "isolated polynucleotide" and "isolated nucleic acid segment" as used herein shall mean a polynucleotide of genomic, cDNA, or synthetic origin or some combination thereof, which by virtue of its origin the "isolated polynucleotide" or "isolated nucleic acid segment" (1) is not associated with all or a portion of a polynucleotide in which the "isolated polynucleotide" or "isolated nucleic acid segment" is found in nature, (2) is operably linked to a polynucleotide which it is not linked to in nature, or (3) does not occur in nature as part of a larger sequence.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of murine proteins, (3) is expressed by a cell from a different species, or, (4) does not occur in nature.

The term "polypeptide" as used herein is a generic term to refer to native protein, fragments, or analogs of a polypeptide sequence. Hence, native protein, fragments, and analogs are species of the polypeptide genus.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "recombinant" in the context of polypeptide coding regions and the polypeptides encoded by such coding regions refers to non-native products wherein the coding regions, and typically the expression thereof, have been manipulated in vitro by man to differ from their occurrence in nature. The viral capsid polypeptides utilized in the methods of the present invention may be produced in a number of different recombinant systems known in the art, including but not limited to, archeal, prokaryotic, or eukaryotic systems. In particular, but not by way of limitation, bacterial, yeast, baculovirus, and mammalian vectors and corresponding host organisms may be utilized according to methods known in the art. For expression in an appropriate expression system, the desired viral capsid polypeptide coding regions are operably linked into an expression vector and introduced into a host cell to enable expression. The coding region with the appropriate regulatory regions will be provided in proper orientation and reading frame to allow for expression. Methods for gene construction are known in the art. See, in particular, Molecular Cloning, A Laboratory Manual, Sambrook et al, eds., Cold Spring Harbor Laboratory, Second Edition, Cold Spring Harbor, N.Y. (1989) and the references cited therein.

The terms "substantial increase" and "substantial decrease", as well as grammatical equivalents thereof, will be understood herein to refer to at least a 30% increase or decrease, such as at least a 50% increase or decrease, at least a 75% increase or decrease, or at least a 90% increase or decrease.

The term "juxtaposed" as used herein will be understood to mean to place close together or side by side. When juxtaposed, two molecules are in "close proximity" to one another. The distance over which the molecules must be in proximity to each other to be considered in "close proximity" to one another so as to be juxtaposed can vary, depending on the requirements of the fluorescent labels utilized, as described in more detail herein below.

Turning now to the methods of the present invention, disclosed and claimed herein are methods of identifying compounds that interfere with protein aggregation, such as but not limited to, viral capsid assembly.

The methods of the present invention may be utilized to identify potential antiviral compounds directed against any virus that requires assembly of a protein coat for function/infection, and for which an in vitro assembly system is available. For example, but not by way of limitation, the method of the present invention may be utilized to identify potential antiviral compounds directed against HIV, hepatitis B, hepatitis C, influenza, SARS, alpha viruses such as West Nile, St. Louis encephalitis, Western and Eastern equine encephalitis, picornaviruses such as hepatitis A and polio, Herpes, and the like.

The method of the present invention involves first identifying at least one capsid polypeptide, wherein at least one of the C-terminus and the N-terminus of the capsid polypeptides are in close proximity to one another when the capsid polypeptides are assembled into the capsid. This condition is typical for most viruses. Next, an amount of capsid polypeptide necessary for performing a desired number of in vitro assembly reactions is purified and then labeled at the appropriate terminus with a fluorescent dye that changes fluorescence at high concentration, such as but not limited to, self-quenches at high concentration. An in vitro assembly reaction is prepared utilizing the labeled capsid polypeptides, assembly is induced, and an amount of fluorescence is detected at at least one time point following induction of assembly. The induction of assembly is detected as a change in the fluorescence of the sample. When the fluorescent dye self-quenches at high concentration, the induction of assembly is detected as a decrease in the fluorescence of the sample. Then, one or more in vitro assembly reactions are prepared and conducted under the same conditions as described above, but in the presence of at least one test compound. The in vitro assembly reactions in the presence and absence of the at least one test compound may be conducted simultaneously or consecutively. The ability of the at least one test compound to inhibit, enhance or misdirect assembly of the capsid polypeptides into the virus capsid is detected by an effect on the change in fluorescence when compared to the in vitro assembly reaction containing capsid polypeptide alone. When the fluorescent dye self-quenches at high concentration, the ability of the test compound to inhibit assembly is detected as a decrease in the chance in fluorescence, and the ability of the test compound to enhance or misdirect assembly is detected as an increase in the change in fluorescence and/or as an increase in the rate at which the change in fluorescence occurs.

The capsid polypeptides utilized in accordance with the present invention are capable of forming a virus capsid in an in vitro assembly reaction. When the virus capsid is formed, at least one of the N-terminus and C-terminus of one of the capsid polypeptide molecules is in close proximity to the N-terminus or C-terminus of another capsid polypeptide molecule. The required distance over which the termini must be in "close proximity" will vary depending on the label attached thereto; however, this distance will be such that a change in the fluorescence of the label can be detected between capsid polypeptide present free in solution and capsid polypeptide assembled in capsid form. Utilization of any capsid polypeptides that can function in accordance with the present invention and are known in the art, falls within the scope of the present invention. Examples of capsid polypeptides that may be utilized in the methodology of the present invention include, but are not limited to, capsid polypeptides of human immunodeficiency virus, Dengue fever virus, West Nile virus, hepatitis C virus, Norwalk virus, parvoviruses, reoviruses, and the like. While certain capsid polypeptides are described in detail herein below, it is to be understood that the present invention is not limited to the particular embodiments disclosed in the Examples, and that a person of ordinary skill in the art, given the present disclosure, can readily identify capsid polypeptides that may be utilized in accordance with the methods of the present invention.

The test compound may be any compound which can be added to a viral in vitro assembly reaction and for which it is desired to know whether such compound interferes with viral capsid assembly. One of the advantages of the present invention is that the potential toxicity of the test compound is not a factor. The prior art methods of detecting compounds that inhibit virus assembly are performed in tissue culture or animal models, and thus are dependent on bioavailability and toxicity of the compound; however, the methods of the present invention are independent of bioavailability and/ortoxicity of the test compound. Therefore, researchers are able to screen for classes of small molecules with limited bioavailability or poor toxicity profiles to identify molecular targets. This increases the range of families of compounds and the specificity of the test, while decreasing the actual number of compounds to be tested. Any lead compounds identified in this in vitro screen can be improved subsequently by medicinal chemists to improve activity and utility as a therapeutic.

In vitro assembly reaction reagents are widely known and commercially available for a variety of viruses. However, methods of constructing in vitro assembly reactions are also within the skill of a person of the art, and therefore the scope of the present invention is not strictly limited to the reactions described herein or currently available in the art; rather, any in vitro assembly reaction constructed by a person of ordinary skill in the art based on common knowledge in the art and without requiring undue experimentation falls within the scope of utilization with the methods of the present invention.

The in vitro assembly reactions may be conducted in a high throughput screening assay, such as in a 96-well plate format, thus allowing for the screening of multiple test compounds, multiple concentrations of each test compound, and multiple control reactions, including but not limited to, standard curves of un-assembled labeled capsid polypeptide and standard curves of labeled capsid polypeptide. In addition, different assembly induction conditions (such as but not limited to, different salt concentrations) may be screened. Also, fluorescence may be read at several different time points to ensure completion of assembly in the reactions.

In one embodiment, the capsid polypeptide may be recombinantly produced. The recombinant capsid polypeptide may be genetically modified to enable labeling thereof. In one embodiment, the recombinant capsid polypeptide is modified to include a cysteine residue at the N- or C-terminus thereof. The method may further include modifying other native cysteines in the capsid polypeptide (such as by mutating the cysteines to alanine), if they are not necessary for function of the capsid polypeptide, so that they do not interfere with labeling of the modified cysteine. Modification of other native cysteines in the capsid polypeptide may be useful if such native cysteines are either accessible to free dyes or are not involved in stable disulfide bonds.

In another embodiment, rather than adding a cysteine to the capsid polypeptide, the N-terminal amine of the capsid polypeptide may be directly and specifically labeled. For example but not by way of limitation, if the N-terminal amine has a pK of about 7, it may be labeled utilizing succinimide or cyanylation chemistry. Methods of labeling amines utilizing such chemistries are known in the art (see, for example, the Molecular Probes Catalog), and therefore no further discussion of such labeling methods is considered necessary.

In yet another embodiment, the C-terminus of the capsid polypeptide may be labeled using, for example but not by way of limitation, carbodiimide chemistry. Methods of labeling the C-terminus of a polypeptide are known in the art, and therefore no further discussion of such labeling methods is considered necessary.

The recombinantly produced, modified capsid polypeptide is then purified and labeled, such as but not limited to, with a self-quenching fluorophore.

A fluorophore may be employed in the methods of the present invention and detected via any of numerous colorimetric and fluorescence detection methods. Depending on the application and purpose, such methods include, but are not limited to, absorbance spectroscopy, fluorescence spectroscopy, fluorescence activated cytometry (FACS), fluorescence microscopy, fluorescence resonance energy transfer (FRET), and the like.

Various types of fluorophores, depending on the application and purpose, may be employed in accordance with the present invention. Examples of suitable fluorophores include, but are not limited to, BODIPY®FL (Invitrogen/ Molecular Probes, Carlsbad, Calif.), rhodamine, pyrene, any one of the FRET pairs shown in Table I, and the like.

Ample guidance regarding fluorophore selection, methods of linking fluorophores to various types of molecules, and methods of use thereof is available in the literature of the art [for example, refer to: Richard P. Haugland, "Molecular Probes: Handbook of Fluorescent Probes and Research Chemicals 1992-1994", 5th ed., Molecular Probes, Inc. (1994); U.S. Pat. No. 6,037,137 to Oncoimmunin Inc.; Hermanson, "Bioconjugate Techniques", Academic Press New York, N.Y. (1995); Kay M. et al., 1995. Biochemistry 34:293; Stubbs et al., 1996. Biochemistry 35:937; Gakamsky D. et al., "Evaluating Receptor Stoichiometry by Fluorescence Resonance Energy Transfer," in "Receptors: A Practical Approach," 2nd ed., Stanford C. and Horton R. (eds.), Oxford University Press, UK. (2001); U.S. Pat. No. 6,350,466 to Targesome, Inc.]. Therefore, no further description is considered necessary.

In some instances, multiple fluorescent labels are employed. In one embodiment, at least two fluorescent labels are used which are members of a fluorescence resonance energy transfer (FRET) pair. FRET is a phenomenon known in the art wherein excitation of one fluorescent dye is transferred to another without emission of a photon. A FRET pair consists of a donor fluorophore and an acceptor fluorophore. The fluorescence emission spectrum of the donor and the fluorescence absorption spectrum of the acceptor must overlap, and the two molecules must be in close proximity. The distance between donor and acceptor at which 50% of donors are deactivated (transfer energy to the acceptor) is defined by the Forster radius ($R_o$), which is typically 10-100 Å. Changes in the fluorescence emission spectrum comprising FRET pairs can be detected, indicating changes in the number that are in close proximity (i.e., within 100 Å of each other). This will typically result from the binding or dissociation of two molecules, one of which is labeled with a FRET donor and the other of which is labeled with a FRET acceptor, wherein such binding brings the FRET pair in close proximity. Binding of such molecules will result in an increased fluorescence emission of the acceptor and/or quenching of the fluorescence emission of the donor.

In another aspect of FRET, a fluorescent donor molecule and a nonfluorescent acceptor molecule ("quencher") may be employed. In this application, fluorescent emission of the donor will increase when quencher is displaced from close proximity to the donor and fluorescent emission will decrease when the quencher is brought into close proximity to the donor. Useful quenchers include, but are not limited to, DABCYL, QSY 7 and QSY 33.

Examples of FRET pairs (donor/acceptor) useful in the methods of the present invention are disclosed in Table I. However, this list is not to be considered exhaustive, and other examples of FRET pairs that may be utilized in accordance with the present invention will be known to those of ordinary skill in the art.

TABLE I

FRET Pairs Useful in the Methods of the Present Invention

| Fluorescent Donors and Acceptors | |
|---|---|
| EDANS | fluorescein |
| IAEDANS | fluorescein |
| fluorescein | tetramethylrhodamine |
| fluorescein | LC Red 640 |
| fluorescein | Cy 5 |

TABLE I-continued

FRET Pairs Useful in the Methods of the Present Invention

| | |
|---|---|
| fluorescein | Cy 5.5 |
| fluorescein | LC Red 705 |
| Fluorescent Donor and NonFluorescent Acceptor (Quencher) | |
| EDANS | DABCYL (4-((4-(dimethylamino)phenyl)azo)benzoic acid, succinimidyl ester) |
| Texas Red | DABCYL |
| BODIPY ® | DABCYL |
| Lucifer yellow | DABCYL |
| coumarin | DABCYL |
| fluorescein | QSY 7 dye |

While one particular method of modifying a capsid polypeptide to enable labeling thereof has been described herein, it is to be understood that the invention is not limited to this particular example, and other methods of modifying polypeptides to enable attachment of fluorescent labels are well known in the art and also fall within the scope of the present invention.

In addition, while fluorescence resonance energy transfer (FRET) is described herein as one method of detecting inhibition, enhancement or misdirection of viral assembly, other methods of detecting same can be utilized in accordance with the present invention, including but not limited to exciplex formation, which utilizes pyrene labels that are particularly appropriate for examining assembly of membrane bound proteins.

While the methods of the present invention have been described in detail for use in detecting compounds that interfere with viral assembly, it is to be understood that the present invention is not limited to such embodiment. Also included within the scope of the present invention are methods of detecting compounds that inhibit any type of protein aggregation or self-association of proteins, such as but not limited to, self association of membrane bound proteins; aggregation of molecules in diseases, such as but not limited to Alzheimers, Huntingtons, and sickle cell; and the like.

The present invention also includes kits for use with the methods described herein. The kits of the present invention may include an amount of labeled capsid polypeptide, wherein when the capsid polypeptide assembles into a viral capsid, at least one of the C-terminus and the N-terminus of the capsid polypeptides are in close proximity to one another, and wherein the labeled capsid polypeptide is labeled with a fluorescent dye that changes fluorescence at high concentration. In one embodiment, the fluorescent dye self-quenches at high concentration. The kit may also include means for screening multiple test compounds simultaneously. Such means may include any plate or other apparatus used for high throughput screening, as described herein and known in the art.

One of the advantages of methods of the present invention is the adaptability of the methods to high-throughput screening. In addition, the methods of the present invention can be performed without regard for bioavailability and/or toxicity of the test compound, whereas current prior art methods utilize tissue culture or animal models which require information of the toxicity of the compound prior to performing the assay, and that prevent the use of some compounds.

In addition, the methods of the present invention are much faster than prior art methods; assembly may be followed in real time, and plate containing in vitro assembly reactions performed in accordance with the present invention may be read in a fluorometer/plate reader minutes after initiating assembly. In contrast, tissue culture assay require at least 3-5 days and complicated assays for their performance. Further, some prior art methods utilize ELISA assays, which require conformationally specific monoclonal antibodies and which have a limited linear range. In contrast, the methods of the present invention are robust assays over a wide range of assembly conditions, and are scalable to very small volumes for high throughput screening. Finally, the methods of the present invention allow for the detection of both inhibition and enhancement of virus assembly, both of which are deleterious to a virus.

Examples are provided hereinbelow. However, the present invention is to be understood to not be limited in its application to the specific experimentation, results and laboratory procedures. Rather, the Examples are simply provided as one of various embodiments and is meant to be exemplary, not exhaustive.

EXAMPLE 1

HBV is a serious public health problem worldwid1, with more than 400 million people chronically infected by this small enveloped DNA virus. HBV has an icosahedral core, comprising viral nucleic acid and reverse transcriptase, enclosed in a protein capsid composed of 240 copies of the capsid (or core) protein. Core assembly is essential for replication, as DNA synthesis occurs exclusively within the core particle. HBV capsid assembly has been studied extensively by the inventor in vitro using the N-terminal assembly domain (residues 1-149) of strain adyw capsid protein expressed in *Escherichia coli* (Wingfield et al., 1995). This protein lacks the C-terminal nucleic acid binding domain (residues 150-183), dispensable for assembly of empty capsids (Nassal, 1992). The HBV capsid protein is a dimer in solution (Wingfield et al., 1995; and Zhou et al., 1992). In vitro assembly of HBV capsid protein depends on protein concentration, NaCl concentration, pH and temperature (Wingfield, et al., 1995; Zlotnick et al., 1999; and Ceres, et al., 2002), and is probably regulated allosterically (Ceres, et al., 2002; Stray et al., 2004; and Stray et al., 2005). Assembly is nucleated by a trimer of core-protein dimers, followed by rapid addition of subsequent dimers (Zlotnick et al., 1999). A network of weak intersubunit contacts holds HBV capsids together (Ceres et al., 2002), a property common to many virus systems (Zlotnick, 2003). Capsids persist even under unfavorable conditions because disassembly and reassembly reactions compete, leading to a kinetic barrier to dissociation (hysteresis) (Singh, 2003).

Heteroaryldihydropyrimidines (HAPs) (Weberet al., 2002; and Deres et al., 2003), initially discovered in a tissue culture-based screen, have recently been shown to inhibit HBV replication by perturbing capsid assembly (Stray et al., 2005; and Hacker et al., 2003). In vitro assembly is accelerated in the presence of HAP-1, a representative HAP compound, leading to aberrant particles (sheets and tubes) at higher HAP-1 concentrations. This suggests that HAPs act as synthetic allosteric activators. HAP-1 also reorganized core protein from preassembled capsids into noncapsid polymers, presumably by interaction of HAP-1 with dimers freed during capsid 'breathing', the transitory breaking of individual intersubunit bonds (Stray et al., 2005).

To more readily identify assembly-directed molecules, the present invention is directed to an in vitro system for assessing the ability of small molecules to alter HBV capsid assembly. The presently claimed and disclosed invention demonstrates the sensitivity of this assay using small molecules that prevent normal HBV capsid assembly, either by inhibiting capsid formation (urea (Singh et al., 2003)) or by accelerating and misdirecting assembly (HAP-1 (Stray et al., 2005)).

Capsid assembly causes core-protein C termini to be brought close together, suggesting that distance-sensitive probes such as the fluorescent BODIPY dyes could be attached at the C terminus and undergo self-quenching when assembly occurs. Cryo-lectron microscopy studies have shown that the C termini of C150 are located on the interior of the assembled capsid and are in close proximity (Zlotnick et al., 1997). This has been supported in an X-ray crystal structure (1QGT) (Wynne et al., 1999), although density halted short of the C termini. Measured from the last modeled amino acids in 1QGT, distances between C termini of adjacent subunits range from 12.3 Å to 14.8 Å. Distances across the fivefold and sixfold vertices range from 17.3 Å to 21.6 Å; the remaining six to seven disordered residues could easily allow substituents at the C termini to collide across a vertex. By comparison, within a dimer, the last ordered C-terminal residues are about 50 Å apart.

For fluorescent labeling, the mutant C150 (Zlotnick et al., 1997; SEQ ID NO:1) was chosen, where all wild-type cysteines have been mutated to alanines, and a unique cysteine was added to the C terminus, thus allowing facile labeling with cysteine-reactive agents. All of the cysteine residues of the HBV core protein are dispensable for core assembly, DNA replication and particle production (Nassal, 1992). C150 was nearly quantitatively labeled with BODIPY-FL maleimide (C150BO). Dimeric C150BO was highly fluorescent, but fluorescence was markedly reduced when C150BO was assembled (FIG. 1).

Figure 2:
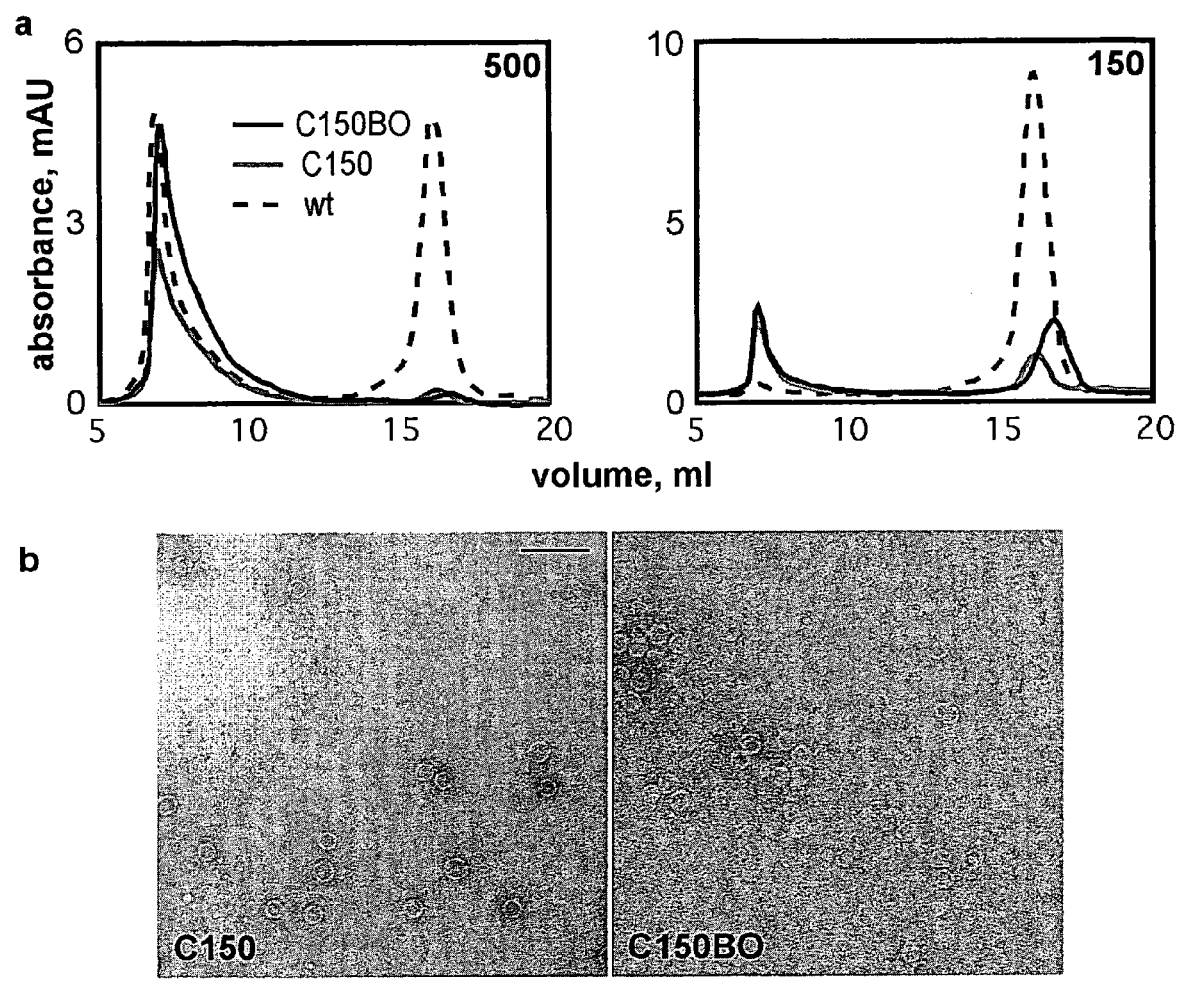
FIG. 2 illustrates assembly of C150BO. (a) Assembly reactions containing 4 µM wildtype Cp149 (dashed line), unlabeled C150 (gray), and BODIPY-labeled C150 (solid) assembled 24 h at 23° C. were analyzed by size exclusion chromatography on a Superose 6 column. C150 and C150BO assemble to a greater extent than does wildtype, as seen from the reduction in size of the dimer peak (see also Table II). The capsid peaks for C150 and C150BO were slightly broadened at 0.5 M NaCl suggesting more intermediates; this was exacerbated at higher temperature or [NaCl]. Accumulation of intermediates, likely a kinetic trap, may be related to the greater association energy for C150BO. (b) Electron micrographs of unlabelled C150 (left) and C150BO (right), assembled with 0.5 M NaCl as in panel (a), showed numerous spherical particles with little evidence of aberrant assembly.

Self-quenching of BODIPY dyes occurs by formation of a ground-state dimer (Bergström, et al., 2002). This non-fluorescent dimer can also act as an acceptor for fluorescence resonance energy transfer, further quenching fluorescence (Johnson et al., 1991). The absorbance spectrum of the unassembled C150BO dimer is typical for the BODIPY-FL monomer, but the assembled C150BO shows a reduction in the absorbance of the BODIPY-FL peak at 504 nm and a shoulder at 477 nm, qualitatively consistent with the presence of BODIPY-FL dimers (Bergström et al., 2002) (FIG. 2).

The assembly of HBV capsid protein has previously been characterized by the inventors using real-time 90° light scattering and size-exclusion chromatography (SEC) (Ceres et al., 2002; Stray et al., 2004; Stray et al., 2005; and Ceres et al., 2004). In the present invention, assembly of C150BO was tested by light scattering using a range of NaCl concentrations (FIG. 1a). In parallel experiments, C150BO was tested for assembly by light scattering and BODIPY-FL fluorescence. The rate and extent of assembly increased with increasing NaCl concentration, as seen with the wild type, whereas fluorescence decreased (FIG. 1b).

Figure 3:
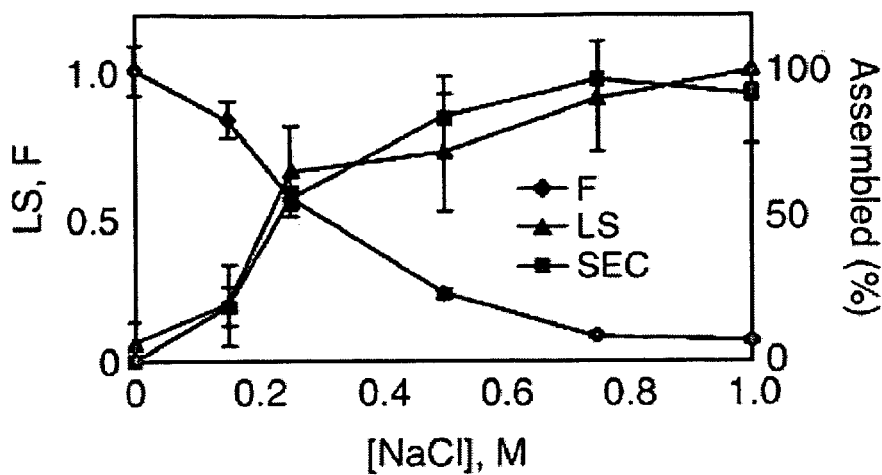
FIG. 3 illustrates that fluorescence quenching correlates with size-exclusion chromatography at equilibrium. Assembly reactions containing 3 µM C150BO and the indicated concentrations of NaCl were analyzed by fluorescence, 90° light scattering or size-exclusion chromatography at 24 h. Assembly reactions appeared to have equilibrated by this time. Note that fluorescence and light scattering data were normalized to their maximum values (at 0 NaCl for fluorescence, at 1 M NaCl for light scattering) for ease of comparison. Assembly data are expressed as total protein present in assembly products (capsid plus intermediate). Data are average±standard deviation of three replicates, including samples from FIG. 1. All fluorescence measurements were made in black 96-well fluorescence plates. LS, light scattering; F, fluorescence.

Comparison of assembly kinetics by light scattering and fluorescence (FIG. 1a,b) shows that the curves were essentially identical when rescaled (FIG. 1c), even during the earliest phases of the reaction. Most data points lie on the diagonal when plotting light scattering versus fluorescence over 100 s to 600 s (FIG. 1d). The slopes of the fluorescence versus light scattering curves were the same for [NaCl] $\leq 0.75$ M, indicating a strong correlation between the signals. To compare fluorescence quenching to the extent of assembly at equilibrium, fluorescence and light scattering were measured for overnight assembly reactions (conditions as for FIG. 1); subsequently, each sample was subjected to SEC (FIG. 3). C150BO assembly was more complete than wild-type assembly under the same conditions (Ceres et al. 2002); thus, association energy is slightly higher for C150 and C150BO (Table II and FIG. 4). BODIPY-FL labeling did not significantly affect assembly. Fluorescence, light scattering and SEC measurements of assembly at equilibrium were self-consistent. Assembly increased over the range 0-0.75 M NaCl, whereas fluorescence decreased proportionally over this same range owing to quenching of the dye-labeled molecules.

TABLE II

Comparison of capsid stability ($K_Dapp$)[1] of Cp149 wild-type and C150BO.

| | [NaCl], mM | | | | |
|---|---|---|---|---|---|
| | 150 | 300 | 500 | 700 | 750 |
| Cp149[2] | 14 | 1.9 | 1.8 | 0.77 | |
| C150BO | 2.4 ± 0.2 | 1.3 ± 0.1 | 0.5 ± 0.4 | | 0.1 ± 0.05 |

[1]$K_Dapp$ (apparent $K_D$) can be calculated from the association energy, or estimated from assembly isotherms as the point where dimer and capsid concentrations are equal (Zlotnick, 1994).
[2]Data from Ceres et al., 2002.

Figure 4:
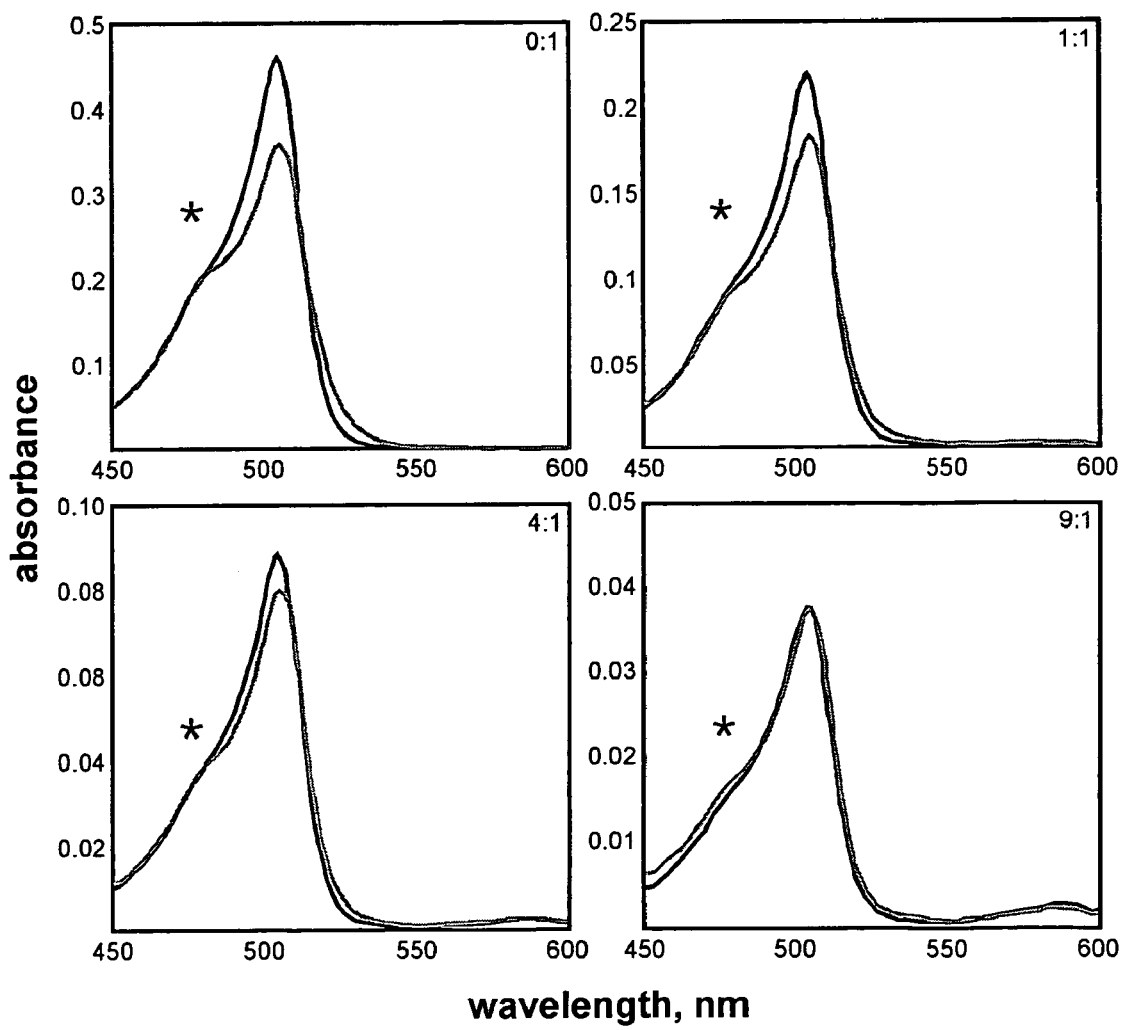
FIG. 4 illustrates absorbance of assembled and unassembled C150:C150BO mixtures. Absorbance of mixtures of unlabelled C150 and C150BO dimers (3.6 µM total protein) were measured over 450-600 nm, either after 16 h of assembly (grey) at 500 mM NaCl at 23° C., or mock assembled (diluted with buffer only, black). Molar ratios of C150 to C150BO are noted on each set of spectra. Absorbance at 477 nm (asterisk), corresponding to BODIPY dimers (Previsani et al., 2002), was more prominent in assembled capsids than in unassembled C150BO dimers. The major BODIPY absorbance peak at 504 nm was reduced upon assembly. In kinetic experiments, absorbance at 504 nm decreased over time, whereas absorbance at 477 nm was essentially unchanged (not shown). The changes in absorbance are qualitatively similar to, but distinct from those previously observed (Bergström, et al., 2002).

SEC of C150BO assembly reactions showed intermediates not usually seen in wild-type assembly reactions; intermediates were less evident at [NaCl]$\leq 0.5$ M (FIG. 4). Similar SEC profiles were seen with unlabeled C150, suggesting that the mutations in C150 differentially affect nucleation of assembly, especially at high NaCl concentrations, leading to kinetic traps as predicted when association energy is increased (as observed in the present invention) and/or nucleation no longer effectively limits the rate of assembly (Zlotnick et al., 1999; and Stray et al., 2004). Unlike fluorescence, light scattering continues to increase at [NaCl]$\geq 1$ M, probably owing to aggregation of kinetically trapped intermediates.

Figure 5:
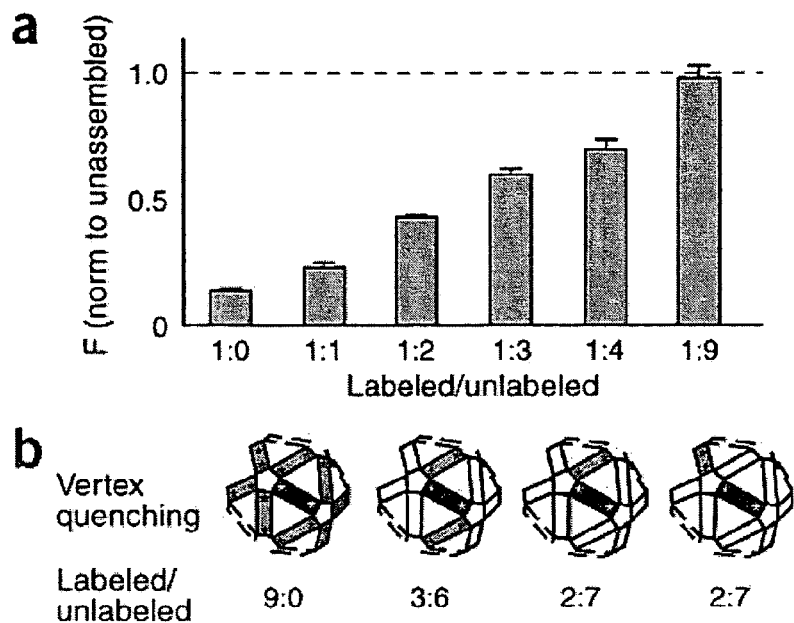
FIG. 5 illustrates that quenching is dominated by interactions between dimers in trans, and occurs across vertices. (a) Assembly reactions (in triplicate) containing mixtures of dye-labeled and unlabeled C150 were performed in 96-well fluorescence microtiter plates and assayed for fluorescence at 24 h. Total protein concentration (labeled plus unlabeled) for each was 3 µM; final NaCl concentration was 1 M, at which assembly was expected to be almost complete (see Table II). To account for the differing amount of dye-labeled protein in each condition, fluorescence of assembled material was normalized to fluorescence of the mock-assembled control for each condition (dimeric C150 and C150BO without NaCl). The dotted line indicates the fluorescence of the mock-assembled control. (b) Cartoon of fluorescence quenching, using a T=1 30-dimer assembly model (Zlotnick, 2005). Dye-labeled subunits are depicted in black or gray, with stars indicating the approximate position of the dye label. Any two dye-labeled subunits meeting at a vertex will quench; that is, the fluorescence of the black dimer can be quenched by any dye-labeled dimer (gray) meeting it at a vertex (solid-edged rectangles). A T=4 or T=3 HBV capsid would have 12 fivefold and 30 or 20 sixfold vertices, respectively.

To better understand fluorescence quenching in C150BO assembly, a series of assembly reactions were constructed containing the same total protein but different proportions of dye-labeled and unlabeled protein (FIG. 5a). Assembly results in little quenching in a 1:9 mixture of C150BO and C150. At this ratio, few capsid vertices have more than one fluorophore, eliminating intradimer quenching (cis quenching) during assembly. For higher proportions of dye-labeled molecules ($\geq 1:4$), quenching is enhanced (FIG. 2). Thus, quenching is dominated by interactions between dye molecules conjugated to different dimers (trans quenching).

The present invention suggests that quenching in trans is due to interactions between two or more BODIPY-FL molecules at a vertex (FIG. 5b). In the capsid, a dimer extends from a fivefold to a sixfold vertex or between two sixfolds, so that each dimer at a vertex will have four or five neighbors. Thus, some quenching will occur when at least one other dye-labeled subunit (gray) is among the subunits meeting the black subunit at a vertex. Thus, a ratio of greater than 1:4 labeled/unlabeled dimer is needed for substantial quenching. Quenching was observed herein with the 1:4 mixture of labeled/unlabeled protein. If quenching could only occur between adjacent molecules, at least two labeled subunits in five would have to be labeled to induce quenching.

The ability of the assay to detect compounds that alter HBV core-protein assembly in vitro was tested by comparing fluorescence data to SEC data for assembly reactions containing either HAP-1 (Stray et al. 2005) or urea (Singh et al., 2003). HAP-1 enhanced the rate and extent of HBV core protein assembly in vitro over a broad range of concentrations (Stray et al., 2005). Higher HAP-1 concentration (≧10 M; that is, >1 HAP-1 molecule per dimer) led to the formation of aberrant particles owing to HAP-1's preference for capsid-protein hexamers rather than pentamers (Stray et al., 2005). The decrease in fluorescence shows that HAP-1 substantially increased both the rate and the extent of C150BO assembly even at substoichiometric levels (FIG. 6a), as seen for the wild-type capsid protein.

Urea inhibits HBV capsid assembly at concentrations ≧0.75 M and causes reversible dissociation of wild-type HBV capsids at concentrations between 2.5 and 3.5 M without denaturing core-protein dimers (Singh et al., 2003). A decrease in assembly by SEC and an increase in fluorescence (loss of fluorescence quenching) was observed in the presence of urea. C150BO still eluted as an apparent dimer by SEC at urea concentrations ≧0.75 M, demonstrating that the inhibition of assembly observed was not due to protein denaturation. It was noted that low levels of HAP-1 or urea had intermediate effects on quenching.

To control for the possibility that either HAP-1 or urea was affecting BODIPY-FL fluorescence, the fluorescence of mock-assembled C150BO dimer without NaCl was assayed. For HAP-1, these controls showed that the drug had no effect on fluorescence at early times (up to 2 h), even though the same amount of HAP-1 had a very strong effect on fluorescence of NaCl-induced assembly at the same times (data not shown). Therefore, the effect on fluorescence was due solely to increased assembly rather than to the drug quenching the fluorescence directly. After 24 h, the HAP-1 mock-assembled controls showed both BODIPY-FL quenching and assembly by SEC, consistent with the previous observation of slow assembly of wild-type capsid protein in the presence of HAP-1 under otherwise nonpermissive conditions (Stray et al., 2005). In the mock-assembled controls, urea affected neither assembly nor quenching.

The BODIPY-FL fluorescence quenching assay was useful in identifying both misdirectors and inhibitors of HBV capsid-protein assembly. BODIPY-FL fluorescence was sensitive to subtle enhancement or inhibition, as well as more substantial effects. Using a 96-well format, a pool of potential small-molecule inhibitors was also tested. A weak misdirector was identified, matching the results we obtained by more labor-intense means (data not shown). Therefore, this assay has potential in rapid screening for pharmaceutical lead compounds.

Exploitation of nonenzymatic aspects of the viral life cycle as therapeutic targets has begun only recently (see de Clercq, 2004 for review). Targeting processes such as virus entry, virion assembly and maturation, particle release and capsid uncoating is problematic because they are less readily assayed. Virus assembly is an integral part of the viral life cycle but has no similarity to processes in the uninfected cell (Zlotnick et al., 2003); thus it should provide a specific target for antiviral therapy. Very small changes in local conformation can cause massive changes in global capsid conformation, leading to aberrant products even though intersubunit interactions in each case are apparently very similar (Stray et al., 2005). This conformational flexibility leaves assembly particularly susceptible to inhibition and/or misdirection.

Figure 6:
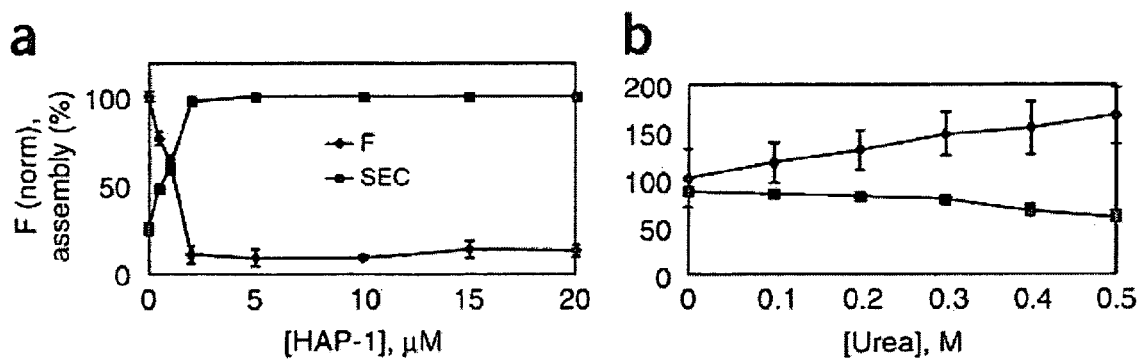
FIG. 6 illustrates that fluorescence quenching in a microtiter plate format is sensitive to assembly misdirection and inhibition. (a) Assembly reactions containing 3 µM C150BO and 150 mM NaCl at 21° C. plus HAP-1 were assayed by fluorescence or size-exclusion chromatography at 24 h. HAP-1 enhanced assembly, leading to enhanced quenching. (b) Assembly reactions containing 3 µM C150BO and 0.5 M NaCl at 21° C. plus urea, which inhibited assembly, were assayed by fluorescence or size exclusion chromatography at 24 h. No reduction in fluorescence due to either inhibitor was observed in mock assembly reactions at early times (2 h, data not shown), demonstrating that neither HAP-1 nor urea had intrinsic quenching activity. Analysis of mock assembly reactions by SEC showed that HAP-1 alone at low salt concentrations was able to induce slow C150BO assembly (data not shown), as seen for wild-type core protein (Stray et al., 2005). Levels of urea were not sufficient to denature dimers (data not shown). All fluorescence measurements were made in black 96-well fluorescence microtiter plates.

The present invention demonstrates a simple, rapid and sensitive fluorescence-based assay for HBV capsid assembly that is readily adaptable to a microtiter plate format and can be scaled up for high-throughput screening. The dynamic range of this assay allows us the detection of both subtle and drastic effects on assembly (FIGS. 1 and 6). This assay can be used to detect both inhibitors, which prevent or prematurely terminate capsid assembly, and misdirectors, which can hyperactivate capsid assembly leading to loss of regulation and/or the formation of aberrant products. An in vitro system has the advantage of rapidity (2-24 h as opposed to 5-7 d) and low cost compared to the currently available tissue culture model. An ex vivo system also enables identification of lead compounds otherwise rejected because of problems with uptake or toxicity, but which may be useful after chemical modification.

Assembly can be monitored in vitro by other techniques, but none of these can be conveniently performed on large numbers of replicate samples, and each has its own technical difficulties. For example, light scattering and turbidity measurements are extremely sensitive to particulates and large aggregates. Enzyme-linked immunosorbent assays are only possible for systems in which assembly-specific antibodies (such as anti-HBcAg) have been characterized. The fluorescence-quenching assay is rapid, works in a microtiter plate format, and is not sensitive to particulates, intermediates or aggregates. As molecular details of assembly are understood for more viruses, this approach is adaptable to avian influenza (Harris et al., 2001), hepatitis C virus (Kunkel et al., 2001), HIV (Campbell et al., 1995) or any other viral system in which the accurate assembly of macromolecular complexes is essential for propagation or infection.

Methods for Example 1

Mutagenesis: For simplicity of chemical labeling, the cysteine residues (C48, C61 and C107) in the assembly domain of HBV strain adyw core protein (amino acids 1-149 (Zlotnick et al., 1996), core protein 149) were mutated to alanine, inserting a unique cysteine residue at the C terminus (C150). Mutagenesis was performed using QuikChange Multi (Stratagene). Mutagenic primers are described in Table III (IDT DNA technologies). Mutations were confirmed by dye terminator dideoxy sequencing (DNA Sequencing Core, Oklahoma Medical Research Foundation). The resulting mutant protein is referred to herein as C150.

TABLE III

Mutagenic Primers.

| Mutation | Primer[1] | SEQ ID NO: |
|---|---|---|
| C48A | CTCCTGAGCACGCCAGCCCTCACCATAC | 2 |
| C61A | GCAATTCTTGCCTGGGGAGACTTAATGACTC | 3 |
| C107A | GTGGTTTCACATTTCTGCTCTCACTTTTGGAAG | 4 |
| insC150 | GGAGACTACGGTTGTT*TGC*AAGGATCCGGCTGC | 5 |

[1]Mutated Codons are underlined. Inserted codons are shown in bold italic.

Protein expression, purification and dye labeling: Wild-type and mutant truncated HBV capsid protein dimers were expressed and purified from *E. coli* as described in Zlotnick et al., 1996 and Zlotnick et al., 2002. Protein was quantified by absorbance at 280 nm ($\epsilon$=60,900 $M^{-1}$ $cm^{-1}$). DTT levels were maintained at 5 mM throughout purification and storage. Immediately before derivatization, C150 protein was removed from storage buffer by chromatography over a G25 PD10 desalting column (Amersham Biosciences) equilibrated with ice-cold 50 mM HEPES pH 7.5 without DTT.

Peak fractions were reacted with BODIPY-FL maleimide (Invitrogen/Molecular Probes) on ice at a final concentration of 4 mM from a 20 mM BODIPY-FL stock in DMSO. Most complete labeling was achieved by overnight reaction, although significant labeling could be achieved by reaction for as little as 10 min. Unreacted dye was removed by separation over a G25 PD10 desalting column equilibrated in ice-cold 50 mM HEPES, pH 7.5. The degree of dye labeling was determined using absorbance at 504 nm ($\epsilon 504=73,000$ M$^{-1}$ cm$^{-1}$, $\epsilon 280=1,300$ M$^{-1}$ cm$^{-1}$). The extinction coefficient was calculated by determining the degree of labeling of BODIPY-FL-labeled C150 preps by MALDI-TOF mass spectrometry. Yield of BODIPY-FL-labeled C150 was typically on the order of 1.9 moles of dye per mole of dimer. Labeling of C150 with fluorescein maleimide was compared to BODIPY-FL; BODIPY-FL conjugates gave a much stronger assembly-dependent change in fluorescence than did fluorescein. Random labeling of $\alpha$ and $\epsilon$ amino groups with succinimidyl conjugates was inefficient, and the labeled proteins showed little or no change in fluorescence on assembly.

Fluorescence and light scattering: Assembly was monitored by fluorescence using a SPEX Fluoromax-2 fluorometer (Horiba Jobin Yvon), using a 0.3-cm path-length cuvette (Hellma) or in black 96-well COSTAR fluorescence microtiter plates (Corning) using a MicroMax adaptor. Assembly reactions were performed at 21° C. Assembly was initiated manually by mixing core protein in 50 mM HEPES, pH 7.5, with buffered NaCl (Sigma) as appropriate. Fluorescence was excited at 504 nm and emission was measured at 509 nm (1-nm band pass for each). For static measurements, all measurements were recorded in triplicate. Qualitatively similar results were obtained using excitation at 495 nm and emission at 512 nm (commonly used for fluorescein fluorescence). Measuring fluorescence of the same reactions in either a cuvette or a 96-well fluorescence microtiter plate gave identical quenching values.

Where assembly was monitored by 90° light scattering, excitation and emission were set at 400 nm with a 3-nm band pass using a 0.3-cm path length cuvette as previously described (Zlotnick et al., 1999; and Stray et al., 2005). Light scattering was measured at 400 nm, rather than 320 nm as previously, to minimize the effect of absorbance of both HAP-1 and BODIPY-FL at the shorter wavelength. The intense scattered light was attenuated by a neutral density filter. Light scattering was monitored in real time during an assembly reaction, or determined in triplicate after 24-h incubation under assembly conditions.

Size-exclusion chromatography: Assembly reactions were examined by SEC on a Superose 6 10/30 column (Amersham Biosciences) mounted on a Shimadzu high-performance liquid chromatography system equipped with an auto injection module (Shimadzu). The column was equilibrated with 50 mM HEPES, pH 7.5, 50 mM NaCl. Recovered protein was assigned either to the void (6.5-7.0 ml), capsid (7.0-8.3 ml), dimer (15-16.5 ml) or intermediate elution (8.3-15 ml).

EXAMPLE 2

Utilizing the methods described herein above in Example 1, several other compounds were tested for their ability to interfere with HBV capsid assembly utilizing in vitro assembly reactions with the labeled capsid polypeptide C150BO.

The assays were carried out as described in Example 1, except as described herein after. Samples were read in 3 minute intervals for one hour and again at 24 hours using a Tecan filter-based plate reader with a standard fluorescein filter set.

Figure 7:
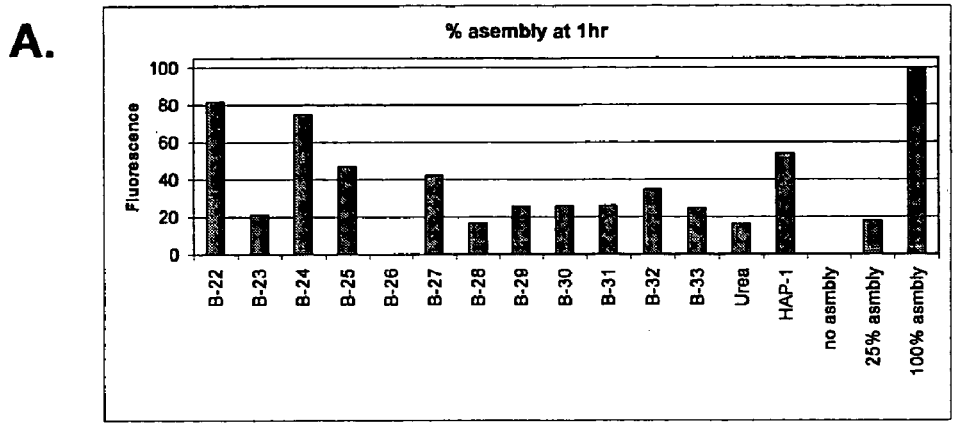
FIG. 7 illustrates an experiment comparing the effects of different compounds( including some heteroaryldihydropyrimidine (HAP) derivatives) on assembly of HBV capsid. Panel A illustrates the effects of the compounds shown in Panel B on % assembly at 1 hour, as detected by fluorescence levels as described herein.
Figure 7:
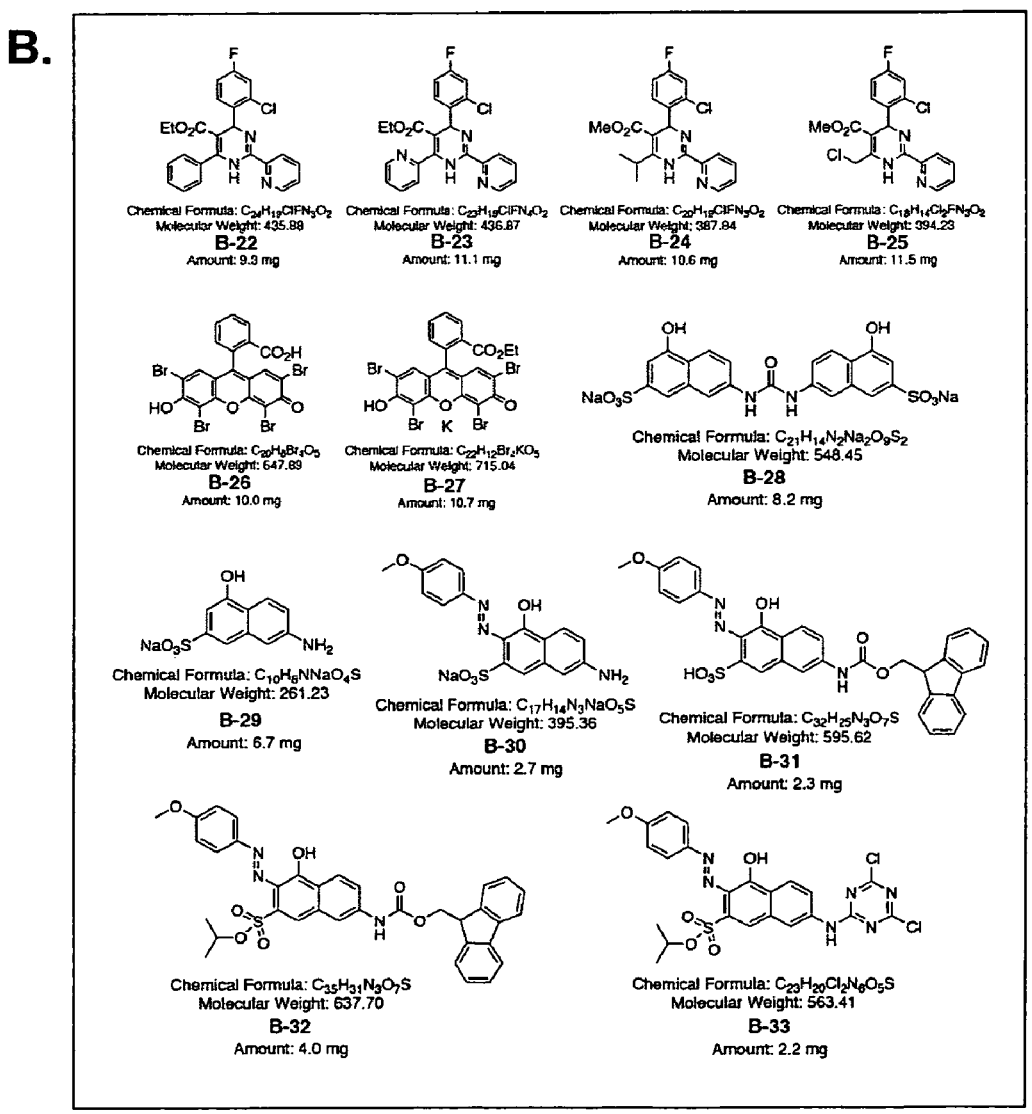

FIG. 7 illustrates a typical experiment comparing different compounds, including some heteroaryldihydropyrimidine (HAP) derivatives. In this experiment, assembly conditions induced 25% (±5%) assembly in the absence of drugs. Compounds B-22, B-24, B-25, and the non-HAP compound B-27 significantly enhanced assembly. Under these conditions, the urea control experiment only showed marginal assembly inhibition.

EXAMPLE 3

The protocols described above in Examples 1 and 2 were developed for a mutant HBV core protein in which the native cysteines were eliminated and a C-terminal cysteine was appended. Because the assays of the present invention are applicable to any virus, or protein, for which there is an in vitro assembly assay, this example provides methods for adapting the above-described assays to other systems. For almost every virus, assembly juxtaposes the N- or C-termini of the capsid proteins (see the VIPER database for examples (Reddy, 2001), making these ends particularly suitable for labeling. It is not necessary to mutate native cysteines if they are not accessible to free dyes; this may occur when the native cysteines are inaccessible to solvent or are already tied up in stable disulfides. Accessibilty of native cysteines can be tested using Eliman's reagent (see below). An N- or C-terminal cysteine can be incorporated using standard molecular biological techniques. As an alternative to cysteine, the N-terminal amine of a protein (if it is not modified) has a pK of about 7 and in some cases can be specifically labeled using succinimide chemistry.

If the labeled ends of the protein are not very close to one another in the assembled protein, detection of assembly using BoDIPY-FL will not work. At that point it becomes necessary to investigate alternative dyes.

To test for free cysteines using Ellman's reagent, the following steps are utilized. A 20 mM stock of Ellman's reagent (dithionitrobenzoic acid, Sigma-Aldrich, St Louis) is prepared by dissolving xmg in a minimum volume of acetone and then adding deionized water to a final volume of 1 ml. For this assay, it is necessary to remove any exogenous reducing agent and transfer the protein to a slightly basic buffer, such as but not limited to 50 mM sodium borate pH 8.5, which can easily be accomplished using a desalting column (see below). The protein stock concentration is then determined by absorbance. It is advisable to have at least 10 µM protein for this assay. The protein's extinction coefficient at 280 nm can be estimated by scoring 7300 M$^{-1}$ cm$^{-1}$ for each tryptophan, 1500 M$^{-1}$ cm$^{-1}$ for each tyrosine, and 100 M$^{-1}$ cm$^{-1}$ for each phenylalanine (see www.expasy.com). To minimize use of protein in this and the next step, black masked 100 µl microcuvettes (Hellma) with a 1 cm optical path length may be used. A blank and the protein sample are then prepared by mixing 100 µl of buffer or protein solution with 20 µl of Ellman's reagent stock solution. After 20 minutes, the absorbance is read at 412 nm. Ellman's reagent modifies free cysteine and releases one thionitrobenzoate, which has an e412 of 17,800 M$^{-1}$ cm$^{-1}$ Keeping in mind the 6/5 dilution (and assuming a 1 cm cuvette), the concentration of thiol in the protein sample is:

$$[thiol] = 6/5 * (A_{412,protein} - A_{412,blank})/17,800 \text{ M}^{-1} \text{ cm}^{-1}$$

This should be compared to the protein concentration to determine the number of solvent accessible cysteines per protein.

Troubleshooting: Alternative dyes. BoDIPY-FL quenching is dependent on formation of a ground state dimer; therefore, it can only be used if assembly places labels in contact with one another. Numerous other dyes with maleimide functional groups (all from Invitrogen/ Molecular Probes) can be considered. Pyrene also depends on formation of a ground state complex but is more hydrophobic. The target protein can also be modified with FRET (fluorescence resonance energy transfer) pairs, though the assay will be dependent on the juxtaposition of distinctly different dyes. Common FRET pairs are described in detail herein above and include, but are not limited to, fluorescein and rhodamine. Unlike the BoDIPY dyes, the absorbance and fluorescence of most fluorophores are exquisitely sensitive to environment.

When labeling protein, it is critical that all column chromatography be performed at 4° C. In addition, if this protocol is being adapted to a different protein, it is critical to remember that maleimides will react with nucleophillic (unprotonated) amines and will preferentially react with the unprotonated form of cysteine. Thus, it is best to maintain the solution between pH 6.5 and 8 using a buffer that does not depend on a primary amine.

To label a protein with BoDIPY-FL, a 50 mM stock of maleimidyl BoDIPY-FL dye is prepared by dissolving xmg of maleimidyl BoDIPY-FL (Invitrogen-Molecular Probes, Eugene, Oreg.) in x$\mu$l of dry DMSO. Stocks may be stored at −80° C. for at least 6 months with little loss of activity. DTT is removed from the protein stock (typically 1.5 mg/ml, 45 $\mu$M) by desalting on a PD10 (GE biosciences) or equivalent Sephadex G25 column (GE Life Sciences, Piscataway, N.J.) equilibrated with ice-cold 50 mM HEPES pH 7.5. 0.5 ml fractions are collected and pooled based on absorbance at 280 nm. The protein is then typically diluted by ⅓, and the protein concentration determined by absorbance at 280 nm ($\epsilon$=60,900 $M^{-1}$ $cm^{-1}$). A black masked 100 $\mu$l microcuvettes (Hellma) with a 1 cm optical path length may be used.

In a 1.5 microcentrifuge tube, 0.8 ml of protein is mixed with 0.2 ml of stock maleimidyl BoDIPY-FL so that there is about a 20 fold molar excess of dye. The tube is covered with aluminum foil to protect it from light, and it is incubated overnight at 4° C. DMSO and unreacted dye are then removed from the solution using a PD10 or equivalent column equilibrated with ice-cold 50 mM HEPES pH 7.5. 0.5 ml fractions are collected and then pooled based on absorbance at 504 nm. Labeled protein will appear in the void volume of this mini-column. Many dyes, including BoDIPY-FL, bind size exclusion gels presumably by hydrophobic interactions. As these dyes cannot be efficiently washed off the column, discard the packing (or the entire column) after each use.

The efficiency of labeling is quantified by measuring the absorbance at 280 and 504 nm, A280 and A504. The extinction coefficient for BoDIPY-FL is 73,000 $M^{-1}$ $cm^{-1}$ at 504 nm and 1,300 $M^{-1}$ $cm^{-1}$ at 280 nm. Therefore, the concentration of bound dye in solution is:

[BoDIPY-FL]=$A504$/78,000 $M^{-1}$

The contribution of dye absorbance at 280 nm must be subtracted to determine the concentration of labeled protein:

[C150Bo]=($A280$−[BoDIPY-FL]*1300 $M^{-1}$)/60,900 $M^{-1}$

The number of dyes per C150Bo dimer is [BoDIPY-FL]/[C150Bo]. The C150Bo sample should be visibly green. Typical labeling is greater than 1.7 dyes/dimer. This material is stored at 4° C. Unlike the unlabeled protein, it does not tolerate freezing well.

Troubleshooting: non-specific, non-covalent binding of dye can occur and interfere with assembly screens by affecting the protein, increasing the background and decreasing the dynamic range of the assay. It is usually seen as more than 2 dyes per C150 dimer, or, after 24 hours, the C150Bo sample becomes slightly cloudy and reddish due to aggregation of the free dye. Aggregated dye can be removed by centrifuging the labeled sample for 30' at 20,000 g. Because the dye binds sepharose, non-covalently associated dye can be removed by elution through another sephadex G25 column.

The goal of assaying assembly effectors is to examine the effect of small molecules on assembly. The basic strategy is to preincubate capsid protein with a small molecule and then induce assembly. In the case of HBV, assembly is induced by raising ionic strength. It is straightforward to determine the extent of assembly under a range of protein concentrations and ionic strengths. It is critical to decide how much assembly is needed to obtain interpretable results.

A critical choice in preparing the assays is in choosing the assay conditions based on the types of compounds: inhibitors or enhancers. This is primarily a question of ionic strength. For assembly inhibitors, it is desirable to have $\geq$50% assembly. For assembly enhancers, 25-30% was chosen, based on a standard curve.

Another critical choice in choosing conditions is whether a data analysis endpoint or coarse-grained kinetics is desired. The simplest assay is an endpoint analysis, the extent of assembly at 24 hours. However, because in vivo assembly is sensitive to changes in kinetics and thermodynamics, there is a great deal of information to be obtained by observing the kinetics of assembly. When there are 96 or more samples, it is impractical to induce one reaction at a time. In order to observe kinetics at coarsely sampled times points, conditions must be chosen so that the half time of assembly is on the order of 10 to 20 minutes, which is conveniently consistent with 25-30% assembly.

Both of these critical choices can be made based on a preliminary standard curve as described herein below.

Pretreating plates: this assay depends on keeping all reactants in solution; therefore, plates are pretreated by adding 150 $\mu$l of 2% Carnation dried milk per well and incubating for 2 hours at room temperature. Treated plates are washed extensively with deionized water and shaken dry.

Standard curves for assembly: drugs will be screened under a standard set of conditions. For C150Bo, the $K_D$apparent at 150 mM NaCl is about 4 $\mu$M; at 300 mM NaCl, the $K_D$apparent is approximately 1 $\mu$M. Because there is some batch to batch variation in C150Bo, the $K_D$apparent must be determined empirically. For 150 mM NaCl: Samples (50 $\mu$l) of protein are set up in 50 mM HEPES pH 7.5 in 2 $\mu$M increments from 0 to 12 $\mu$M C150Bo. Assembly is initiated by addition of 50 $\mu$l of 300 mM NaCl in the same buffer. Reactions are mixed by aspiration. As a full-assembly control for the standard curve, triplicates of a sample of 50 $\mu$l of 10 $\mu$M C150Bo are included, and assembly is initiated by mixing 1:1 with 2 M NaCl. For no-assembly controls, 50 $\mu$l of 10 $\mu$M C150Bo is mixed with 50 $\mu$l of 50 mM HEPES. Buffer blanks are also necessary controls. The plates are covered with adhesive tape and allowed to equilibrate at 21° C. in the dark for 24 hours. The adhesive tape is then removed, and the fluorescence is read in a fluorescence plate reader either using a standard fluorescein filter set or setting the excitation wavelength to 495 nm and the emission wavelength to 512 nm. The fluorescence of the full-assembly control should be no more than $\frac{1}{10}$ the fluorescence of the no-assembly control. After background subtraction, the fluorescence data should be normalized to percent assembly.

$$\% \text{ assembly}_{sample} = 100 \times \frac{F_{sample} - F_{full-assembly}}{F_{no-assembly} - F_{full-assembly}}$$

For the screens described herein above, triplicate controls of full-assembly, no-assembly, and buffer background are included.

Assembly reactions. Protein concentrations are chosen where 25-30% assembly is observed, as the best compromise for identifying enhancers and inhibitors and allowing the observation of HBV assembly kinetics. A stock solution of C150Bo is made in 50 mM HEPES. If 30% assembly is achieved at 4 µM dimer, then the stock should be 204% of this concentration (where the 4% accounts for dilution of drug). In practice, we simply use 8 µM. 48 µl of stock is pipetted into each well, and samples are premixed with 10-20 µM compound and incubated for 20 minutes. For screening purposes, the compound should be in molar excess. If samples are hand pipeted: since compound stocks are typically 20 mM in DMSO, an aliquot of this stock is diluted 1:19 with 50 mM HEPES TO 1 mM. Dilution into buffer decreases the amount DMSO added to the reaction. 2 µl of diluted compound or buffer (as a control) is added to each well. For a final concentration of 150 mM NaCl, 50 µl of 300 mM NaCl is added and then mixed by aspirating. The samples are then read as described herein above. For kinetic studies, the fluorescence is read at 5 minute intervals after mixing, and the readings are continued for one hour; the plate is then covered and stored in the dark at 21° C. For the final point in the kinetic experiment and for endpoint analysis, the fluorescence is read after 24 hours.

Data analysis: fluorescence is then converted to % assembly as described herein above.

Troubleshooting: the difference between assembly and capsid formation. Misdirected assembly, assembly of non-capsid polymers is a very desirable outcome for an assembly inhibitor. There is no direct readout for misdirection from this high throughput assay. However, a generalization can be made that misdirected assembly proceeds without "editing" to remove incorrectly incorporated subunits—this lack of editing is most likely when assembly is much faster or much stronger.

Critical choice: choosing a model—No simple model adequately describes a reaction as complex as virus assembly. The reaction is nominally second order as subunits (Endres, 2005), and small complexes of subu its (Zhang, 2006) add to a growing capsid. The result is that kinetics are nominally sigmoidal and slowly, asymptotically approach equilibrium (Zlotnick, 2005)}. For screening purposes, because in one instance it may be desired to develop indices of assembly, a curve fit is proposed with an oversimplified model. A hyperbolic model is suggested as a first approximation.

Hyperbolic curve fits in terms of fluorescence over time ($F_t$) use:

$$F_{time} = F_{init} - (F_{init} - F_{final}) \cdot ((k_t \cdot t)/(1+(k_t \cdot t)))^n.$$

$F_{init}$ is the initial fluorescence of unassembled protein, determined from the no-assembly controls. $F_{final}$ is a fit parameter; a good starting estimate is the fluorescence at 24 hours (1440 minutes). The same curve fit in terms of % assembly is $$\%_{assembly} = \%_{final} \cdot ((k_t \cdot t)/(1+(k_t \cdot t)))^n$$

Where $\%_{final}$ is the maximum assembly, which like $F_{final}$ is a fit parameter that should use assembly at 1440 minutes as an initial value. The time constant, $k_t$, is the time it takes the reaction to achieve 50% of its dynamic range. The exponential term, n, is optional. It can be included to accommodate the fact that assembly kinetics are not hyperbolic; an exponential term allows fitting to kinetics that are sigmoidal, and have either a very long lag phase or are fast and then level off. In some respects it is analogous to a Hill coefficient, needed to fit a cooperative binding isotherm.

Choice of parameters to fit: For fitting raw fluorescence data, $F_{initial}$ is held constant, as it is experimentally determined. $F_{final}$ is allowed to vary; however, to prevent absurd curve fits, it is limited to be less than or equal to the average of the fluorescence at 60 and 1440 minutes. For a $\%_{assembly}$ fit, $\%_{final}$ is adjustable and should have the same characteristics as $F_{final}$, i.e. a starting value of $\%_{assembly}$ at 1440 minutes and a minimum value of the mean of assembly at 60 and 1440 minutes. The time constant, $k_t$, must be allowed to float freely; a useful starting value is 20 minutes. Cooperativity, n, can be held at 1.0 or allowed to freely float.

Curve fitting software: The "solver" add-in for Microsoft EXCEL or Kaleidagraph have routinely been used. However, any curve fitting software known in the art may be utilized.

Reporting data: useful terms are kt, calculated final assembly based on $F_{final}$, cooperativity (n), and the experimentally observed assembly at 24 hours.

Except where assembly is extraordinarily rapid, n≈1. If n>>1, misdirection, or kinetic trapping, is likely.

Thus, in accordance with the present invention, there has been provided a method of identifying compounds that interfere with protein aggregation, such as assembly of a viral capsid, that fully satisfies the objectives and advantages set forth hereinabove. Although the invention has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the invention.

REFERENCES

The following references, to the extent that they provide exemplary procedural or other details supplementary to those set forth herein, are specifically incorporated herein by reference.

Bergström, F. et al. Dimers of dipyrrometheneboron difluoride (BODIPY) with light spectroscopic applications in chemistry and biology. J. Am. Chem. Soc. 124, 196-204 (2002).

Bergström, F. et al. Dimers of dipyrrometheneboron difluoride [BODIPY] with light spectroscopic applications in chemistry and biology. J. Am. Chem. Soc. 124, 196-204 (2002).

Campbell, S. & Vogt, V. Self-assembly in vitro of purified CA-NC proteins from Rous sarcoma virus and human immunodeficiency virus type 1. J. Virol. 69, 6487-6497 (1995).

Ceres, P., Stray, S. & Zlotnick, A. Hepatitis B virus capsid assembly is enhanced by naturally occurring mutation F97L. J. Virol. 78, 9538-9543 (2004).

Ceres, P. & Zlotnick, A. Weak protein-protein interactions are sufficient to drive assembly of hepatitis B virus capsids. Biochemistry 41, 11525-11531 (2002).

Stray, S., Ceres, P. & Zlotnick, A. Zinc ions trigger conformational change and oligomerization of hepatitis B virus capsid protein. Biochemistry 43, 9989-9998 (2004).

de Clercq, E. Antivirals and antiviral strategies. Nat. Rev. Microbiol. 2, 704-720 (2004).

Deres, K. et al. Inhibition of hepatitis B virus replication by drug induced depletion of nucleocapsids. Science 299, 893-896 (2003).

Ganem, D. Hepadnaviridae and their replication in Fields virology (eds. Fields, B. N. et al.) 2703-2737, (Lippincott-Raven Publishers, Philadelphia, 1996).

Hacker, H., Deres, K., Mildenberger, M. & Schroder, C. Antivirals interacting with hepatitis B virus core protein and core mutations may misdirect capsid assembly in a similar fashion. Biochem. Pharmacol. 66, 2273-2279 (2003).

Harris, A., Forouhar, F., Qiu, S., Sha, B. & Luo, M. The crystal structure of the influenza matrix protein M1 at neutral pH: M1-M1 protein interfaces can rotate in the oligomeric structures of M1. Virology 289, 34-44 (2001).

Johnson, I., Kang, H. & Haugland, R. Fluorescent probes incorporating dipyrromethenboron difluoride fluorophores. Anal. Biochem. 198, 228-237 (1991).

Kunkel, M., Lorinczi, M., Rijnbrand, R., Lemon, S. & Watowich, S. Self-assembly of nucleocapsid-like particles from recombinant hepatitis C virus core protein. J. Virol. 75, 2119-2129 (2001).

Nassal, M. Conserved cysteines of the hepatitis B virus core protein are not required for assembly of replication-competent core particles nor for their envelopment. Virology 190, 499-505 (1992).

Nassal, M., Rieger, A. & Steinau, O. Topological analysis of the hepatitis B virus core particle by cysteine-cysteine cross-linking. J. Mol. Biol. 225, 1013-1025 (1992).

Previsani, N. & Lavanchy, D. Hepatitis B (Epidemic and Pandemic Alert and Response, World Health Organization, Geneva, 2002).

Singh, S. & Zlotnick, A. Observed hysteresis of virus capsid disassembly is implicit in fundamental kinetic models of association and dissociation. J. Biol. Chem. 278, 18249-18255 (2003).

Stray, S. et al. A heteroaryldihydropyrimidine activates and can misdirect hepatitis B virus capsid assembly. Proc. Natl. Acad. Sci. USA 102, 8138-8143 (2005).

Summers, J. & Mason, W. S. Replication of the genome of a hepatitis B-like virus by reverse transcription of an RNA intermediate. Cell 29, 403-415 (1982).

Weber, O. et al. Inhibition of human hepatitis B (HBV) by a novel non-nucleosidic compound in a transgenic mouse model. Antiviral Res. 54, 69-78 (2002).

Wingfield, P. T., Stahl, S. J., Williams, R. W. & Steven, A. C. Hepatitis core antigen produced in *Escherichia coli*: subunit composition, conformational analysis, and in vitro capsid assembly. Biochemistry 34, 4919-4932 (1995).

Wynne, S. A., Crowther, R. A. & Leslie, A. G. The crystal structure of the human hepatitis B virus capsid. Mol. Cell 3, 771-780 (1999).

Zhou, S. & Standring, D. N. Hepatitis B virus capsid particles are assembled from core-protein dimer precursors. Proc. Natl. Acad. Sci. USA 89, 10046-10050 (1992).

Zlotnick, A. Are weak protein-protein interactions the general rule in capsid assembly? Virology 315, 269-274 (2003).

Zlotnick, A., Johnson, J. M., Wingfield, P. W., Stahl, S. J. & Endres, D. A theoretical model successfully identifies features of hepatitis B virus capsid assembly. Biochemistry 38, 14644-14652 (1999).

Zlotnick, A. & Stray, S. How does your virus grow? Understanding and interfering with virus assembly. Trends Biotechnol. 21, 536-542 (2003).

Zlotnick, A., Ceres, P., Singh, S. & Johnson, J. M. A small molecule inhibits and misdirects assembly of hepatitis B virus capsids. J. Virol. 76, 4848-4854 (2002).

Zlotnick, A. Theoretical aspects of virus capsid assembly. J. Mol. Recognit. 18, 479-490 (2005).

Zlotnick, A. et al. Localization of the C terminus of the assembly domain of hepatitis B virus capsid protein: implications for morphogenesis and organization of encapsidated RNA. Proc. Nat. Acad. Sci. USA 94, 9556-9561 (1997).

Zlotnick, A. et al. Dimorphism of hepatitis B virus capsids is strongly influenced by the C-terminus of the capsid protein. Biochemistry 35, 7412-7421 (1996).

Zlotnick, A. To build a virus capsid. An equilibrium model of the self assembly of polyhedral protein complexes. J. Mol. Biol. 241, 59-67 (1994).

---

What is claimed is:

1. A method of identifying a compound that inhibits assembly of a viral capsid, the method comprising the steps of:
providing capsid polypeptides labeled with a fluorescent dye that changes fluorescence at high concentration, wherein assembly of the capsid polypeptides into the viral capsid results in juxtaposition of at least one of the N-terminus and C-terminus of the capsid polypeptides, and wherein the fluorescent dye is attached to the at least one N-terminus and C-terminus of the capsid polypeptide;
providing at least one test compound;
performing an in vitro assembly reaction utilizing the labeled capsid polypeptides in the presence of the at least one test compound;
detecting an amount of fluorescence at at least one time point following induction of assembly in the presence of the at least one test compound, wherein the induction of assembly is detected as a decrease in the fluorescence of the sample;
determining whether the fluorescence detected in the presence of the at least one test compound following induction of assembly is increased when compared to the fluorescence detected in the absence of the at least one test compound following induction of assembly, wherein such increase is an indication that the at least one test compound inhibits assembly of the viral capsid.

2. The method of claim 1, wherein multiple test compounds are provided and screened simultaneously.

3. The method of claim 1 wherein, in the step of providing capsid polypeptides, the capsid polypeptides are recombinant polypeptides.

4. The method of claim 3, wherein the recombinant capsid polypeptides are genetically modified to enable labeling thereof.

5. The method of claim 4, wherein the recombinant capsid polypeptides are genetically modified to include a cysteine residue on the N- or C-terminus thereof such that the at least one terminus of the recombinant capsid polypeptides that are in close proximity to one another when assembled into the capsid is provided with the cysteine residue thereon.

6. The method of claim 5, wherein at least one other cysteine present in the recombinant capsid polypeptide is mutated so that it does not interfere with labeling of the modified cysteine.

7. A method of identifying a compound that enhances or misdirects assembly of a viral capsid, the method comprising the steps of:
providing capsid polypeptides labeled with a fluorescent dye that changes fluorescence at high concentration, wherein assembly of the capsid polypeptides into the viral capsid results in juxtaposition of at least one of the N-terminus and C-terminus of the capsid polypeptides, and wherein the fluorescent dye is attached to the at least one N-terminus and C-terminus of the capsid polypeptide;
providing at least one test compound;
performing an in vitro assembly reaction utilizing the labeled capsid polypeptides in the presence of the at least one test compound;
detecting an amount of fluorescence at at least one time point following induction of assembly in the presence of the at least one test compound, wherein the induction of assembly is detected as a decrease in the fluorescence of the sample;
determining whether the fluorescence detected in the presence of the at least one test compound following induction of assembly is decreased when compared to the fluorescence detected in the absence of the at least one test compound following induction of assembly, wherein such decrease is an indication that the at least one test compound enhances or misdirects assembly of the viral capsid.

8. The method of claim 7, wherein multiple test compounds are provided and screened simultaneously.

9. The method of claim 7 wherein, in the step of providing capsid polypeptides, the capsid polypeptides are recombinant polypeptides.

10. The method of claim 9, wherein the recombinant capsid polypeptides are genetically modified to enable labeling thereof.

11. The method of claim 10, wherein the recombinant capsid polypeptides are genetically modified to include a cysteine residue on the N- or C-terminus thereof such that the at least one terminus of the recombinant capsid polypeptides that are in close proximity to one another when assembled into the capsid is provided with the cysteine residue thereon.

12. The method of claim 11, wherein at least one other cysteine present in the recombinant capsid polypeptide is mutated so that it does not interfere with labeling of the modified cysteine.

13. A method of identifying a compound that misdirects assembly of a viral capsid, the method comprising the steps of:
providing capsid polypeptides labeled with a fluorescent dye that changes fluorescence at high concentration, wherein assembly of the capsid polypeptides into the viral capsid results in juxtaposition of at least one of the N-terminus and C-terminus of the capsid polypeptides, and wherein the fluorescent dye is attached to the at least one N-terminus and C-terminus of the capsid polypeptide;
providing at least one test compound;
performing an in vitro assembly reaction utilizing the labeled capsid polypeptides in the presence of the at least one test compound;
detecting an amount of fluorescence at two or more time points following induction of assembly in the presence of the at least one test compound, wherein the induction of assembly is detected as a change in the fluorescence of the sample;
determining whether the change in fluorescence detected in the presence of the at least one test compound following induction of assembly occurs at a faster rate when compared to the fluorescence detected in the absence of the at least one test compound, wherein such increased rate is an indication that the at least one test compound misdirects assembly of the viral capsid.

14. The method of claim 13, wherein multiple test compounds are provided and screened simultaneously.

15. The method of claim 13 wherein, in the step of providing labeled capsid polypeptides, the capsid polypeptides are recombinant polypeptides.

16. The method of claim 15, wherein the recombinant capsid polypeptides are genetically modified to enable labeling thereof.

17. The method of claim 16, wherein the recombinant capsid polypeptides are genetically modified to include a cysteine residue on the N- or C-terminus thereof such that the at least one terminus of the recombinant capsid polypeptides that are in close proximity to one another when assembled into the capsid is provided with the cysteine residue thereon.

18. The method of claim 17, wherein at least one other cysteine present in the recombinant capsid polypeptide is mutated so that it does not interfere with labeling of the modified cysteine.

* * * * *

UNITED STATES PATENT AND TRADEMARK OFFICE
CERTIFICATE OF CORRECTION

PATENT NO. : 7,329,485 B2 Page 1 of 1
APPLICATION NO. : 11/546796
DATED : February 12, 2008
INVENTOR(S) : Adam Zlotnick It is certified that error appears in the above-identified patent and that said Letters Patent is hereby corrected as shown below:

In the Specification:
Column 8, line 59: Delete "ortoxicity" and replace with -- or toxicity --.

Column 12, line 51: Delete "(Weberet" and replace with -- (Weber et --.

Column 13, line 10: Delete "Cyro-lectron" and replace with -- Cyro-electron --.

Column 19, line 40: Delete "microcuvettes" and replace with -- microcuvette --.

Signed and Sealed this

Third Day of June, 2008

JON W. DUDAS
*Director of the United States Patent and Trademark Office*

SEQUENCE LISTING

<160> NUMBER OF SEQ ID NOS: 5

<210> SEQ ID NO 1
<211> LENGTH: 150
<212> TYPE: PRT
<213> ORGANISM: Hepatitis B virus

<400> SEQUENCE: 1

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Ala

```
                35                  40                  45
Ser Pro His His Thr Ala Leu Arg Gln Ala Ile Leu Ala Trp Gly Asp
    50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Ala Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Cys
145                 150

<210> SEQ ID NO 2
<211> LENGTH: 28
<212> TYPE: DNA
<213> ORGANISM: Artificial Sequence
<220> FEATURE:
<223> OTHER INFORMATION: Mutagenic primer for producing C48A mutation in
      Hepatitis B core protein

<400> SEQUENCE: 2
ctcctgagca cgccagccct caccatac                                     28

<210> SEQ ID NO 3
<211> LENGTH: 31
<212> TYPE: DNA
<213> ORGANISM: Artificial Sequence
<220> FEATURE:
<223> OTHER INFORMATION: Mutagenic primer for producing C61A mutation in
      Hepatitis B virus core protein

<400> SEQUENCE: 3
gcaattcttg cctggggaga cttaatgact c                                 31

<210> SEQ ID NO 4
<211> LENGTH: 33
<212> TYPE: DNA
<213> ORGANISM: Artificial Sequence
<220> FEATURE:
<223> OTHER INFORMATION: Mutagenic primer for producing C107A mutation
      in Hepatitis B virus core protein

<400> SEQUENCE: 4
gtggtttcac atttctgctc tcacttttgg aag                               33

<210> SEQ ID NO 5
<211> LENGTH: 33
<212> TYPE: DNA
<213> ORGANISM: Artificial Sequence
<220> FEATURE:
<223> OTHER INFORMATION: Mutagenic primer for constructing insC150
      mutation in Hepatitis B core protein

<400> SEQUENCE: 5
ggagactacg gttgtttgca aggatccggc tgc                               33
```